United States Patent
Park et al.

(10) Patent No.: US 6,645,239 B1
(45) Date of Patent: Nov. 11, 2003

(54) FLEXIBLE AND SELF-EXPANDABLE STENT AND INSERTING DEVICE FOR SUCH STENTS

(76) Inventors: Jae-Hyung Park, 551-6 Banpo-4-dong, Seocho-ku, Seoul (KR), 137-040; Jin-Wook Jung, 1101-19,. Sampung apt. Secho-4-dong, Seocho-ku, Seoul (KR), 137-070; Kyoung-Min Shin, 446-285, Yeonhee-dong, Seodaimun-ku, Seoul (KR), 120-110

( * ) Notice: Subject to any disclaimer, the term of this patent is extended or adjusted under 35 U.S.C. 154(b) by 0 days.

(21) Appl. No.: 10/069,156

(22) PCT Filed: Nov. 19, 1999

(86) PCT No.: PCT/KR99/00697
§ 371 (c)(1),
(2), (4) Date: Jun. 5, 2002

(87) PCT Pub. No.: WO01/12256
PCT Pub. Date: Feb. 22, 2001

(30) Foreign Application Priority Data

Aug. 18, 1999 (KR) ......................................... 1999-34226

(51) Int. Cl.[7] .................................................. A61F 2/06

(52) U.S. Cl. ..................................... 623/1.11; 623/1.22

(58) Field of Search ............................... 623/1.11, 1.12, 623/1.18, 1.19, 1.2, 1.15, 1.16, 1.22; 606/108

(56) References Cited

U.S. PATENT DOCUMENTS

| 5,476,508 | A | * | 12/1995 | Amstrup | 623/1.2 |
| 6,183,508 | B1 | * | 2/2001 | Stinson et al. | 623/1.2 |
| 6,416,536 | B1 | * | 7/2002 | Yee | 623/1.11 |
| 6,500,202 | B1 | * | 12/2002 | Shaolian et al. | 623/1.11 |

* cited by examiner

Primary Examiner—David H. Willse
Assistant Examiner—Hieu Phan
(74) Attorney, Agent, or Firm—Jagtiani + Guttag

(57) ABSTRACT

A stent (5), made of a shape-memory alloy and inserted into a stenosed vessel (50), and a stent foundation device for inserting such a stent (5) into a desired part (52) of the stenosed vessel (50) are disclosed. The stent (5) consists of a net-structural hollow cylindrical body (3) made by knitting one longitudinal superelastic shape-memory alloy wire while repeatedly crossing the wire at various points so as to form a plurality of diamond-shape meshes (2). The stent foundation device consists of an actuation steel core (12), a moveable tube (15) and an insert tube (20), which are received within an outside hollow tube (13) while being axially movable within the outside tube. (13). In the above device, an insert tip (23) is connected to the front end of the insert tube (20). The insert tip (23) has a step (22) forming a fitting end, at which the insert tip (23) is partially fitted into the front end of the outside tube (13) and is connected to the front end of the insert tube (20). A thread (21) is fixed at one end thereof to the insert tube (20) at a position spaced apart from the step (22) of the insert tip (23) by a distance. The above thread (21) holds the stent (5) on the insert tube (20) within the outside tube (13).

7 Claims, 5 Drawing Sheets

FLEXIBLE AND SELF-EXPANDABLE STENT AND INSERTING DEVICE FOR SUCH STENTS

TECHNICAL FIELD

The present invention relates, in general, to a stent made of a shape-memory alloy and inserted into a stenosed vessel, or other part, and a stent foundation device for inserting such a stent into a desired part of a stenosed vessel and, more particularly, to a highly flexible and self-expandable stent used for being inserted into a stenosed vessel, such as a cancer-stenosed esophagus, biliary tract or urethra in addition to a thrombus-blocked vein, so as o artificially restore the stenosed vessel or being used in setting an artificial passage between intrajugular portal veins, the present invention also relating to a stent foundation device used for precisely inserting such a stent into a desired position within the stenosed vessel.

BACKGROUND ART

As we well known to those skilled in the art, blood veins may be stenosed, obstructed or blocked by thrombi or by arteriosclerosis, thus causing a variety of diseases.

In the case of such an angiostenosis, a stenosed vein may be surgically replaced with an artificial vein or may be surgically bypassed.

However, such a surgical operation for treating the angiostenosis is problematic in that it is necessary to but the body of a patent at a large area around stenosed veins and this undesirably leaves a large and ugly scar on the body. The conventional stenosis treating surgical operation also forces the patient to undergo recuperation for a substantially lengthy period of time, nevertheless, possibly failing to provide a desired operational effect.

Particularly, such angiostenoses have been typically caused by a hyperpiesia or heart disease. However, it is impossible to perform such a stenosis treating surgical operation on a patient having the hyperpiesia or the heart disease.

In an effort to overcome such problems derived from the surgical operation for treating the angiostenoses, a vascular restorative surgical operating procedure has been proposed to be used in place of such a conventional surgical operation. In such a vascular restorative surgical operating procedure, a femoral artery is perforated to form a small hole, through which a balloon catheter tube is inserted from the outside of the body of a patient into a desired stenosed part of the vein prior to expanding the balloon within the vein.

However, such a vascular restorative surgical operating procedure is problematic in that the restored vein is typically stenosed again within three or four months after the surgical operating procedure, thus forcing the surgical operating procedure to be repeatedly performed on the patient at three or four month intervals. This makes the patient repeatedly suffer from the surgical operating procedure and repeatedly pay much money for the surgical operating procedure, thus being very inconvenient to the patient.

On the other hand, in the case of an esophagostenosis caused by a cancer, it is impossible for the patient to ingest food through the stenosed esophagus, and so it is necessary to set an ingestion tube directly extending from the exterior of the abdomen into the stomach. However, this forces the patient and his family members to endure great physical hardship.

The conventional surgical operation or the conventional vascular restorative surgical operating procedure has been performed to treat biliary tract stenoses or urethra stenoses, or to set an artificial passage between intrajugular portal veins in addition to the treatment for the stenosed vein or stenosed esophagus.

However, the conventional surgical operation or the conventional vascular restorative surgical operating procedure for treating the stenoses regrettably fails to provide a desired operational effect and regrettably makes the patient and his family members experience great physical hardship while paying much money, thus being very inconvenient to them.

DISCLOSURE OF THE INVENTION

Accordingly, the present invention has been made keeping in mind the above problems occurring in the prior art, and an object of the present invention is to provide a stent, which is made of a superelastic shape-memory alloy and is semipermanently used when it is once set within a desired stenosed vessel of a patient.

Another object of the present invention is to provide a foundation device for such stents, which easily and effectively inserts and sets a stent into and within a desired part of a stenosed vessel of a patient's body, thus restoring the stenosed vessel.

A further object of the present invention is to effectively set a stent within a desired part of a stenosed vessel, thus stretching and restoring the stenosed vessel.

Yet another object of the present invention is to allow a stent to be retracted into an outside tube so as to be reduced in volume and to be precisely reset at a desired position within a stenosed vessel when the stent fails to be precisely set at the desired position within the stenosed vessel.

Still another object of the present invention is to precisely set a stent at a desired position within the stenosed vessel.

Still another object of the present invention is to allow a stent to be semipermanently used when it is once set within a desired stenosed vessel of a patient.

In order to accomplish the above objects, the present invention provides a stent, consisting of a net-structural hollow cylindrical body made by knitting one longitudinal superelastic shape-memory alloy wire while repeatedly crossing the wire at various points so as to form a plurality of diamond-shaped meshes. The present invention also provides a foundation device for inserting such a stent into a stenosed vessel of a patient so as to restore the stenosed vessel. The foundation device consists of an actuation steel core, a movable tube and an insert tube, which are received within an outside hollow tube while being axially movable within the outside tube. In the above device, an insert tip is connected to the front end of the insert tube. The insert tip has a step forming a fitting end, at which the insert tip is partially fitted into the front end of the outside tube and is connected to the front end of the insert tube. A thread is fixed at one end thereof to the insert tube at a position spaced apart from m the step of the insert tip by a distance. The above thread holds the stent on the insert tube within the outside tube.

BRIEF DESCRIPTION OF THE DRAWINGS

The above and other objects, features and other advantages of the present invention will be more clearly understood from the following detailed description taken in conjunction with the accompanying drawings, in which:

FIGS. 1 and 2 are views, showing a stent in accordance with the preferred embodiment of the present invention, in which:

FIG. 1 is a perspective view of the stent; and

FIG. 2 is a front view of the stent;

BEST MODE FOR CARRYING OUT THE INVENTION

Figure 1:
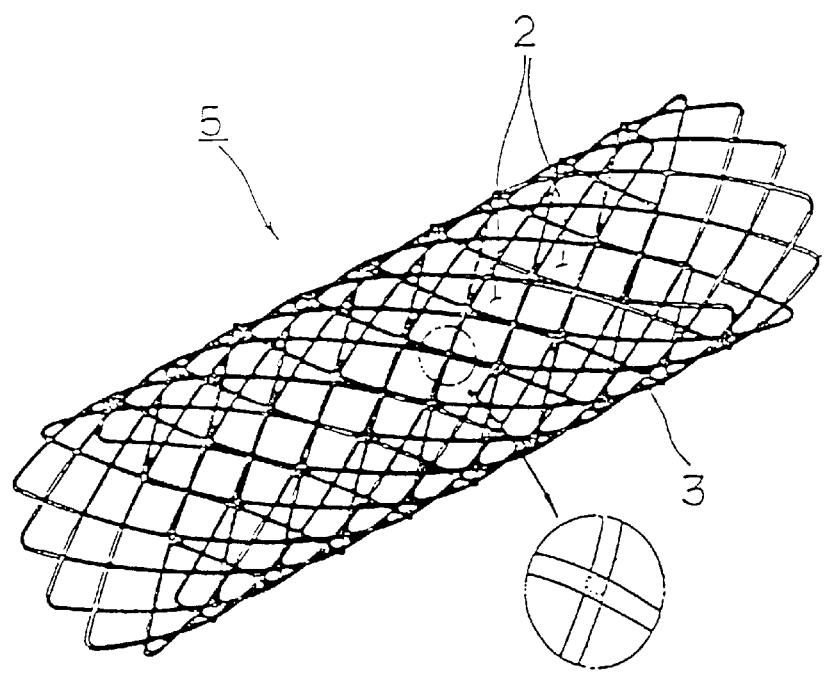
Figure 2:
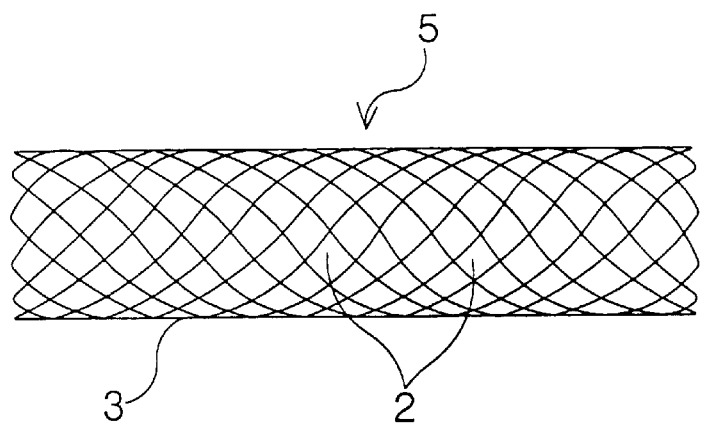
Figure 3:
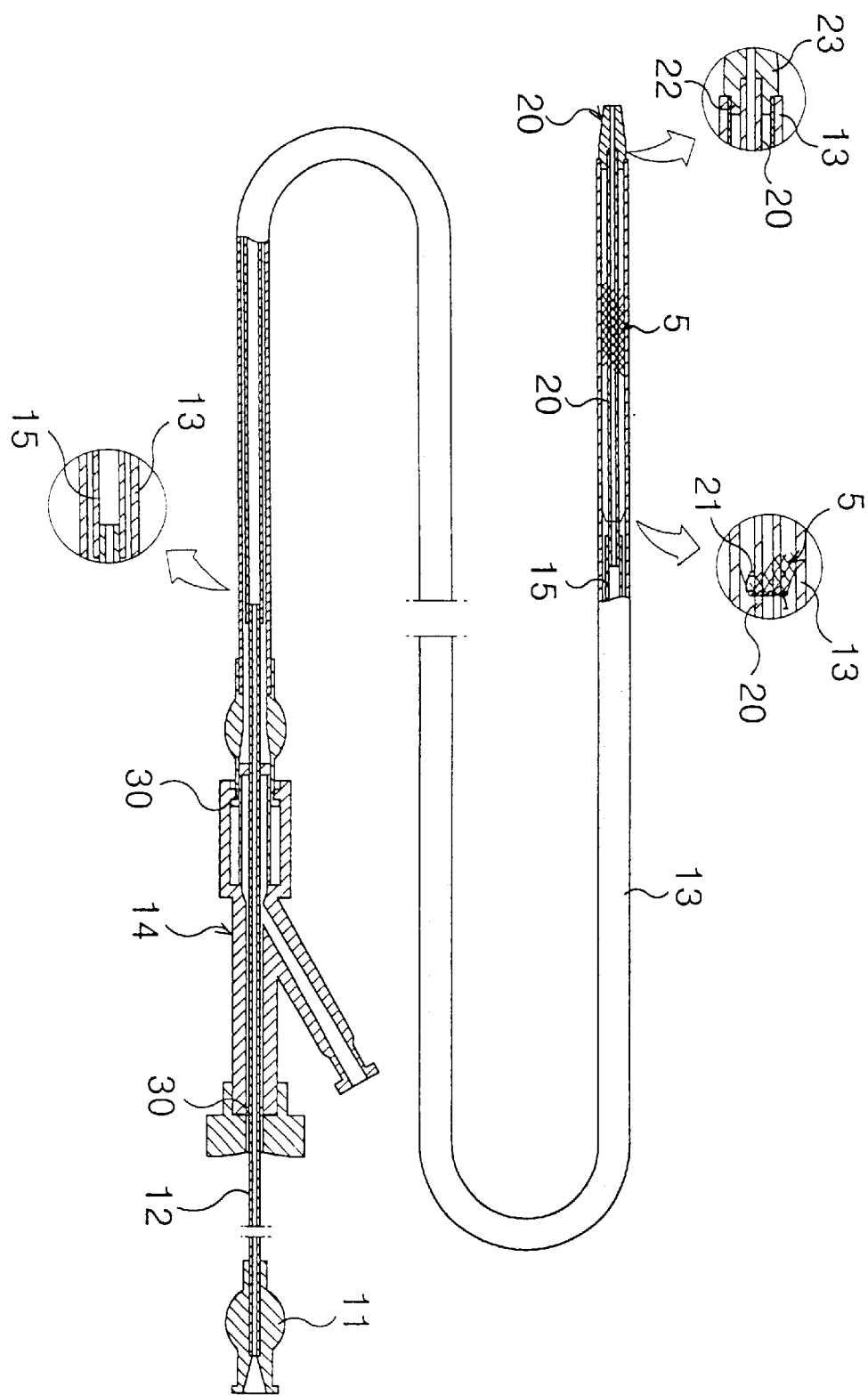
FIG. 3 is a partially sectioned view of a foundation device for scents in accordance with the preferred embodiment of the present invention.

As shown in FIGS. 1 and 2, the stent 5 of the present invention comprises a net-structural hollow cylindrical body 3, which has a predetermined length and is made by knitting one longitudinal superelastic shape-memory alloy wire having a diameter of 0.1 mm~0.5 mm while repeatedly crossing the wire at various points so as to form a plurality of diamond-shaped meshes 2. Each end of the net-structural stent 5 is formed with a plurality of smooth and continuous curves which are spaced apart from each other at regular intervals. After completely knitting the superelastic shape-memory alloy wire into a desired net structural cylindrical body 3, both ends of the wire are positioned within the cylindrical body 3 prior to being welded to the body 3.

In such a case, the stent 5 is designed to have a length longer than a stenosed part 52 of a blood vein 50 and a diameter larger than the inner diameter of the normal vein 50 by 10~30%.

As shown in FIGS. 3 to 7, the foundation device for stents according to this invention comprises an actuator 14 movably enclosing an actuation steel core 12, with an outside hollow tube 13 being hermetically connected to the front end of the actuator 14. A movable tube 15 is connected to the front end of the actuation steel core 12 and is movably enclosed within the outside tube 13, thus being axially movable along the outside tube 13 by the actuation steel core 12.

An insert tube 20 is movably received within the outside tube 13 and is connected to the front end of the movable tube is, thereby being axially movable within the outside tube 13. An insert tip 23 is fixed to the front end of the insert tube 20. The above insert tip 23 has a step 22, thus forming a fitting end at which the tip 23 is partially fitted into the front end of the outside tube 13 and is fixed to the front end of the insert tube 20.

The insert tube 20 is connected to the one end of a thread 21 at a position spaced apart from the step 22 of the insert tip 23 by a distance, thus fixing the end of the thread 21.

In such a case, the thread 21 has an appropriate length which allows the free end portion of the thread 21 to circumferentially and continuously stitch on the stent 5 upwardly and downwardly while passing through the diamond-shaped meshes 2 provided at the rear end of the stent 5.

In the foundation device of this invention, all the outside tube 13, movable tube 15 and insert tube 20 are made of a flexible material.

In the present invention, it is necessary to set the maximum length "L" of the stent 5 expected at a time the stent 5 is fully contracted in diameter so as to be reduced in volume. A plurality of indicator marks 24, with an interval between the outermost marks 24 being equal to the maximum length "L" of the stent 5, are regularly formed on the outside tube 13.

In the drawings, the reference numeral 11 denotes a handle grip, and the numeral 30 denotes a sealing ring accomplishing a desired sealing effect within the actuator 14.

The operational effect of the present invention will be described hereinbelow.

In order to insert the stent 5 into a desired position of a stenosed vessel of a patient's body, it is necessary to primarily install the stent 5 in the foundation device.

Figure 4:
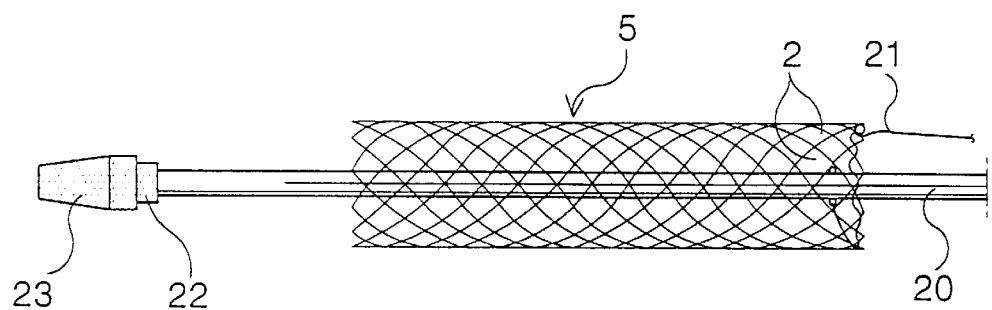
FIGS. 4 to 6 are views, showing a process of installing a stent in the foundation device of this invention.
Figure 5:
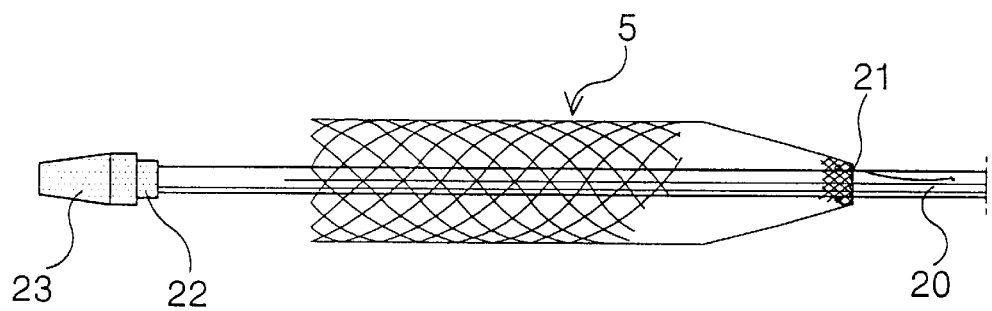
Figure 6:
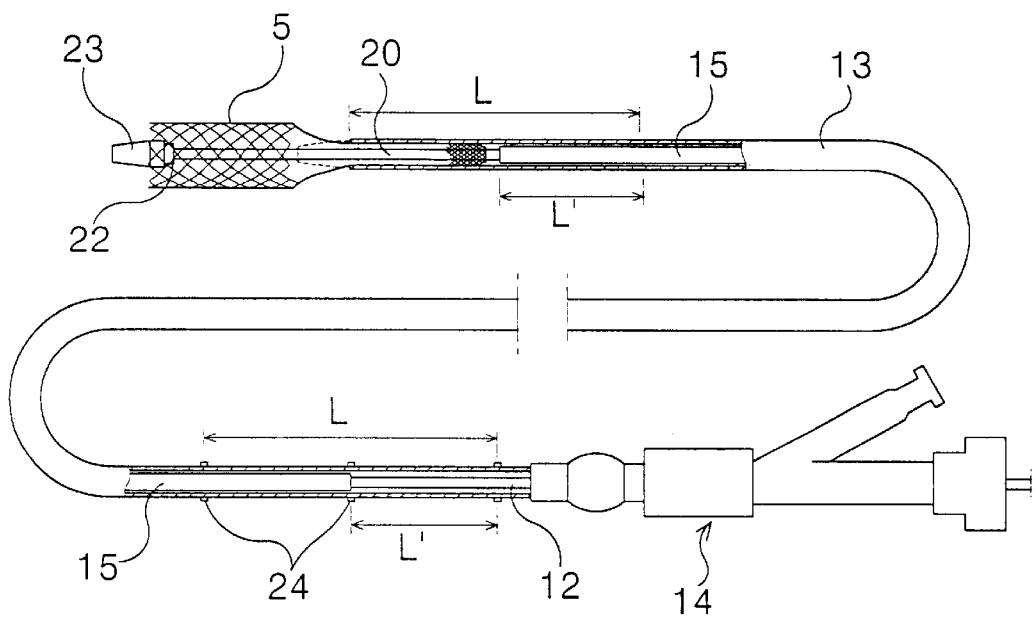

That is, the net-structural cylindrical body 3 of the stent 5 is primarily fitted over the insert tube 20 of the device as shown in FIGS. 4 to 6.

In such a case, the insert tube 20 is in a projected position outside the front end of the outside tube 13.

After the stent 5 is fitted over the insert tube 20 in the protected position of the tube 20, the thread 21, fixed to the insert tube 20 at its fixed end, is circumferentially and continuously stitched on the rear end of the net-structural cylindrical body 3 of the stent 5 upwardly and downwardly at its free end portion while passing through the diamond-shaped meshes 2 provided at the rear end of the stent 5 as shown in FIG. 4.

After the thread 21 is completely and circumferentially stitched on the rear end of the net-structural stent 5, the free end portion of the thread 21 is pulled so as to fully contract the rear end of the stent 5 as shown in FIG. 5. Therefore, the volume of the fully contracted rear end of the stent 5 is reduced to a minimum volume.

When the handle grip 11 is manually and fully pulled, with the volume of the rear end of the stent S being reduced to a minimum volume, all the actuation steel core 12, movable tube 15 and insert tube 20 are moved backwardly within the outside tube 13 by the pulling force of the handle grip 11.

In such a case, the net-structural cylindrical body 3 of the stent 5, connected to the insert tube 20 by the thread 21, is inserted into the outside tube 13 while being reduced in volume to a minimum volume, with the front end of the body 3 being positioned at the step 22 of the insert tip 23.

In the above-mentioned position, the rear end of the net-structural cylindrical body 3 of the stent 5 compresses the stitched thread 21, thus holding the thread 21. Therefore, the stent 5 is firmly connected to the insert tube 20 by way of the thread 21. On the other hand, the front end of the cylindrical body 3 of the stent 5 is squeezed between the step 22 of the insert tip 23 and the outside tube 13 without being exposed to the outside of the insert tip 23.

Figure 7:
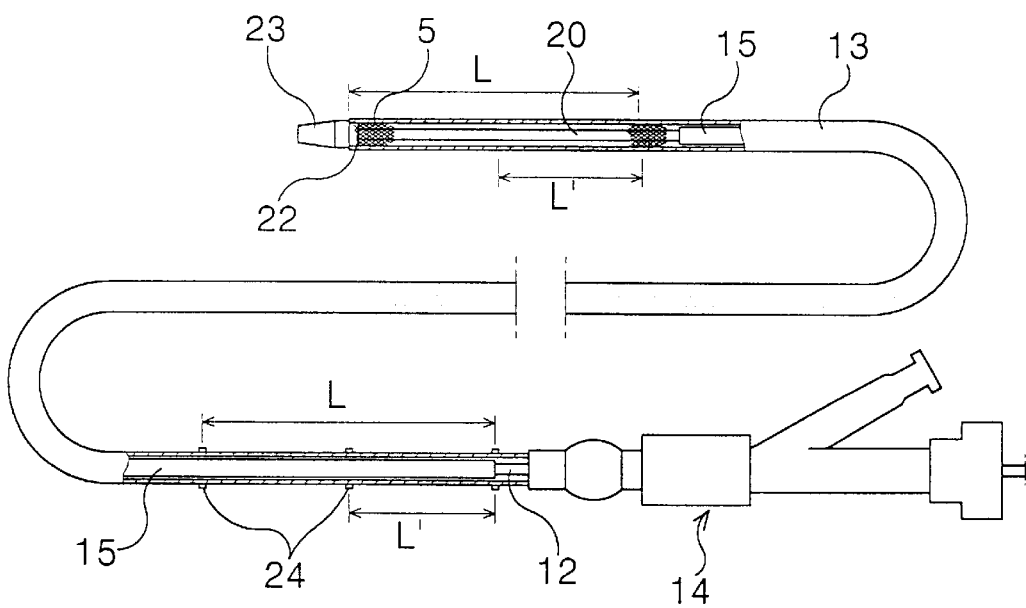
FIG. 7 is a view, showing a stent completely installed in the foundation device of this invention.
Figure 8:
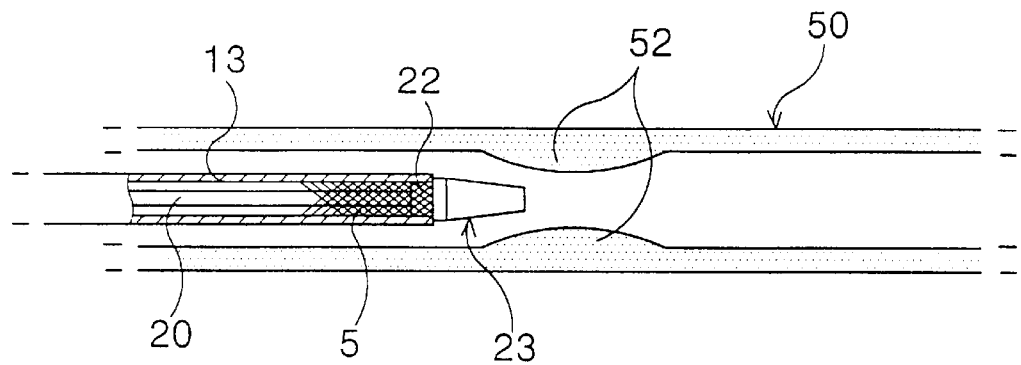
FIGS. 8 to 10 are sectional views, showing a process of setting a stent at a desired position within a stenosed vessel by the foundation device of this invention.
Figure 9:
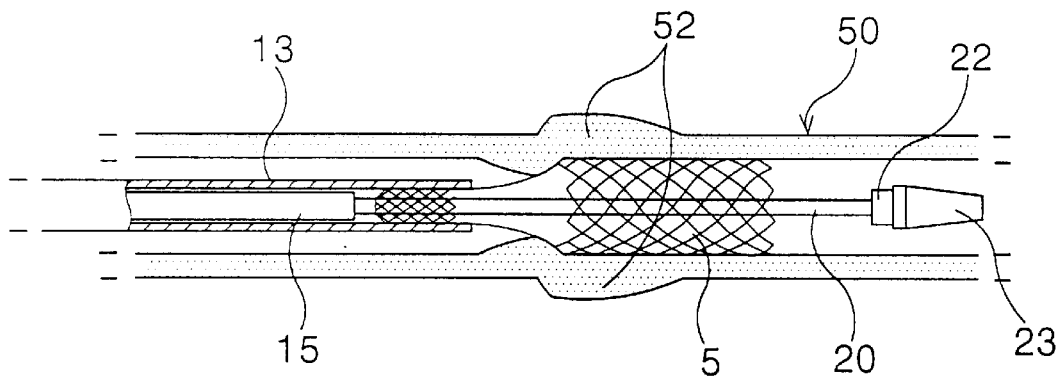
Figure 10:
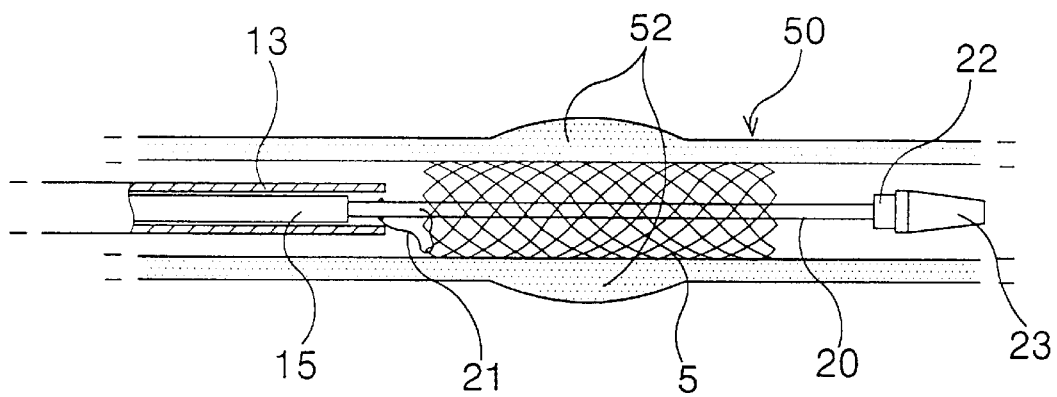

Therefore, the stent 5 is completely installed within the foundation device as shown in FIG. 7. After the installation of the stent 5 in the foundation device, a vascular restorative surgical operating procedure is performed on a patient suffering from an angiostenosis to insert and set the stent 5 into and at a desired position within a stenosed vein.

The insert tip 23 of the foundation device has a truncated conical shape at its distal end, thus being freely and smoothly movable within the veins 50 without generating a resistance during the vascular restorative surgical operating procedure. In addition, all the outside tube 13, movable tube 15 and insert tube 20 are flexible tubes, and so they are smoothly movable within the curved veins 50.

During the vascular restorative surgical operating procedure, all the outside tube 13, movable tube 15 and insert tube 20 are moved along the vein 50 until the insert tip 23 reaches a stenosed part 52 of the vein 50.

When the outside tube 13, movable tube 15 and insert tube 20 are moved along the vein 50, the stent 5 is free from affecting the inside wall of the vein 50 since the net-structural cylindrical body 3 of the stent 5 is completely received within the outside tube 13, with the front end of the cylindrical body 3 being squeezed between the step 22 of the insert tip 23 and the outside tube 13 without being exposed to the outside of the tip 23.

After the insert tip 23 of the device completely reaches the stenosed part 52 of the vein 50, the handle grip 11 is slowly pushed.

When the grip 11 is slowly pushed as described above, all the actuation steel core 12, movable tube 15 and insert tube 20 are moved forwardly within the outside tube 13, thus projecting the insert tube 20 from the front end of the outside tube 13.

When the insert tube 20 is projected from the front end of the outside tube 13, the step 22 of the insert tip 23 fixed to the insert tube 20 is projected from the interior of the outside tube 13 to the outside of the front end of the outside tube 13.

In such a case, the fully contracted stent 5 is gradually projected from the interior of the outside tube 13 to the front end of the tube 13. When the stent 5 is slowly projected from the front end of the outside tube 13, the projected portion of the net-shaped cylindrical body 3 of the contracted stent 5 quickly expands to its original shape due to the characteristics of the superelastic shape-memory alloy. Therefore, the diameter of the projected portion of the body 3 is quickly enlarged.

However, at the above position, the contracted rear end of the cylindrical body 3 is not projected from the front end of the outside tube 13, thus being still held by the stitched thread 21 fixed to the insert tube 21. Therefore, when the insert tube 20 is moved, the cylindrical body 3 of the stent 5 along with the insert tube 20 is moved within the outside tube 13.

During such a stent projecting action of the foundation device, it may be necessary to reset the position of the stent 5 within the vein 50 due to a mis-operation of a surgeon or an undesirable mis-positioning of the stent 5 within the vein 50.

In such a case, it should be understood that the projected stent 5 has to be fully inserted into the outside tube 13 again prior to moving the stent 5 within the vein 5 so as to reset the position of the stent 5. That is, when the projected stent 5 is moved within the vein 5 without being fully inserted into the outside tube 13, the projected end of the net-structural stent 5 may stress or damage the inside wall of the vein 50, thus regrettably making the patient suffer. Therefore, it is necessary to fully insert the projected stent 5 into the outside tube 13 again prior to moving the stent 5 within the vein 5 so as to reset the position of the stent 5. Of course, the stent 5 of this invention is particularly designed to have a plurality of smooth and continuous curves at each end thereof so as to prevent such undesirable stress or damage caused by the projected end of the stent 5.

In order to fully insert the projected stent 5 into the outside tube 13 again prior to moving the stent 5 within the vein 5 so as to reset the position of the stent 5, the handle grip 11 is pulled so as to move all the steel core 12, movable tube 15 and insert tube 20 backwardly within the outside tube 13 by the pulling force of the handle grip 11.

In such a case, the net-structural cylindrical body 3 of the stent 5, connected to the insert tube 20 by the thread 21, is inserted into the outside tube 13 while being reduced in volume to the minimum volume when the insert tube 20 is inserted into the outside tube 13 as described above.

Therefore, the net-structural stent 5 is completely positioned within the outside tube 13 while being fully contracted.

After the stent 5 is completely inserted into the outside tube 13 as described above, the insert tip 23 is precisely positioned at the stenosed part 52 of the vein 50. The handle grip 11 is, thereafter, slowly pushed. All the actuation steel core 12, movable tube 15 and insert tube 20 are thus moved forwardly within the outside tube 13, thus projecting the insert tube 20 from the front end of the outside tube 13.

When the insert tube 20 is projected from the front end of the outside tube 13, the insert tip 23 is projected from the interior of the outside tube 13 to the outside of the front end of the outside tube 13.

The fully contracted stent 5, connected to the insert tube 20 through the thread 21, is thus gradually projected from the front end of the outside tube 13 to the outside of the tube 13 while quickly expanding to its original shape due to the characteristics of the superelastic shape-memory alloy. Therefore, the diameter of the projected portion of the body 3 is quickly enlarged.

When the net-structural cylindrical body 3 of the stent 5 is completely projected from the outside tube 13, the stent 5 completely returns to its original shape and radially expands the stenosed part 52 of the vein 50 outwardly, thus restoring the stenosed part 52.

As described above, the stent 5 is designed to have a length longer than the stenosed part 52 of the vein 50 and a diameter larger than the inner diameter of the normal vein 50 by 10~30%. Therefore, the superelastic stent 5 effectively and uniformly expands the stenosed part 52 of the vein 50 outwardly in a radial direction without moving within the vein 50, thus restoring the stenosed part 52 and maintaining the restored state of the part 52.

After the stent 5 is completely set within the stenosed part 52 of the vein 50, the foundation device is removed from the vein 50, thus finishing the vascular restorative surgical operating procedure for treating the angiostenosis.

When the stent 5 is positioned within the stenosed part 52 while completely and elastically expanding in diameter, the stent 5 releases the thread 21. Therefore, when the insert tube 20 is removed from the vein 50 after finishing the vascular restorative surgical operating procedure, the thread 21 is easily removed from the diamond-shaped meshes 2 of the stent 5 while being trailed by the insert tube 20. The thread 21 is thus completely removed from the vein 50 along with the insert tube 20.

Therefore, only the elastically expanding stent 5 is left within the stenosed part 52 of the vein 50.

The stenosed part 52 of the vein 50 is thus effectively restored by the stent 5.

In the foundation device of this invention, it is preferable to regularly form a plurality of indicator marks 24 on the outside tube 13 so as to allow the marks 24 to be always positioned outside a patient's body.

The object of the indicator marks 24 is to allow a surgeon to precisely push the handle grip 11 to a length equal to a desired projected length of the stent 5 from the outside tube 13, with the stent 5 being completely inserted into the stenosed part 52 of the vein 50.

That is, the above indicator marks 24 are designed to have an interval between the outermost marks 24 equal to the maximum length "L" of the stent 5 expected at a time the stent 5 is fully contracted in diameter so as to be reduced in volume. Therefore, when the actuation steel core 12 is pushed, with a mark of the core 12 being moved from the initial one of the indicator marks 24 to a length L' as shown in FIGS. 4 and 5, the stent 5 is projected from the front end of the outside tube 13 by the length L' while being positioned within the stenosed part 52 of the vein 50.

Therefore, it is possible for a surgeon to exactly know the projected length of the stent 5 from the tube 13 outside a patient's body during a vascular restorative surgical operating procedure for treating the angiostenosis. This finally allows the surgeon to effectively, precisely and safely perform the vascular restorative surgical operating procedure.

Industrial Applicability

As described above, the present invention provides a stent, which is made of a superelastic shape-memory alloy and is semipermanently used when it is once set within a desired stenosed vessel of a patient. The present invention also provides a foundation device for such stents, which easily and effectively inserts and sets a stent into and within a desired part of a stenosed vessel of a patient's body, thus restoring the stenosed vessel.

During a vascular restorative surgical operating procedure for treating an angiostenosis, the stent of this invention is retracted into an outside tube so as to be reduced in volume, and so the stent is easily and effectively inserted and set into and at a desired part of a stenosed vessel. In addition, it is also possible to precisely reset the stent at the desired position within the stenosed vessel when the stent fails to be precisely set at the desired position. This finally allows a surgeon to effectively, precisely and safely perform the vascular restorative surgical operating procedure.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A foundation device for inserting a stent into a stenosed vessel of a patient so as to restore the stenosed vessel, comprising an actuator movably enclosing an actuation steel core, an outside hollow tube hermetically connected to a front end of said actuator, and a movable tube connected to a front end of said actuation steel core and movably received within said outside tube so as to be axially movable along the outside tube by the actuation steel core, further comprising:

an insert tube movably received within the outside tube and connected to a front end of said movable tube, thereby being axially movable relative to the outside tube;

an insert tip connected to a front end of said insert tube, said insert tip having a step forming a fitting end, at which the insert tip is partially fitted into the front end of the outside tube and is connected to the front end of said insert tube; and a thread having a fixed end fixed to said insert tube at a position spaced apart from said step of the insert tip by a distance and having a free end for circumferentially and continuously stitching on said stent upwardly and downwardly while passing through diamond-shaped meshes of said stent when said stent is fitted over said insert tube.

2. The foundation device according to claim 1, further comprising said stent, wherein said stent comprises a net-structural hollow cylindrical body having a predetermined length and being made by knitting one longitudinal superelastic shape-memory alloy wire while repeatedly crossing said wire at various points so as to form a plurality of said diamond-shaped meshes, with each end of said cylindrical body being formed with a plurality of smooth and continuous curves spaced apart from each other at regular intervals, and both ends of said alloy wire being positioned within said cylindrical body and being welded to the cylindrical body after completely knitting the alloy wire into a desired net structural cylindrical body.

3. The foundation device according to claim 2, wherein said thread, connected to said insert tip, is allowed at its free end portion to circumferentially and continuously stitch on the stent upwardly and downwardly while passing through said diamond-shaped meshes provided at a rear end of the stent, said thread thus allowing the stent to be movable along with the insert tube when the stent is completely received within the outside tube while being fully contracted in diameter so as to be reduced in volume.

4. The foundation device according to claim 2, wherein a maximum length of the stent, expected at a time the stent is fully contracted in diameter so as to be reduced in volume, is set, and a plurality of indicator marks, with an interval between outermost indicator marks being equal to said maximum length of the stent, are regularly formed on said outside tube.

5. The foundation device according to claim 1, wherein said thread, connected to said insert tip, is allowed at its free end portion to circumferentially and continuously stitch on the stent upwardly and downwardly while passing through said diamond-shaped meshes provided at a rear end of the stent, said thread thus allowing the stent to be movable along with the insert tube when the stent is completely received within the outside tube while being fully contracted in diameter so as to be reduced in volume.

6. The foundation device according to claim 1, wherein a maximum length of the stent, expected at a time the stent is fully contracted in diameter so as to be reduced in volume, is set, and a plurality of indicator marks, with an interval between outermost indicator marks being equal to said maximum length of the stent, are regularly formed on said outside tube.

7. A stent for inserting into a stenosed vessel of a patient so as to restore the stenosed vessel, comprising:

a net-structural hollow cylindrical body having a predetermined length and being made by knitting one longitudinal superelastic shape-memory alloy wire while repeatedly crossing said wire at various points so as to form a plurality of diamond-shaped meshes, with each end of said cylindrical body being formed with a plurality of smooth and continuous curves spaced apart from each other at regular intervals, and both ends of said alloy wire being positioned within said cylindrical body and being welded to the cylindrical body after completely knitting the alloy wire into a desired net structural cylindrical body.

* * * * *